(12) United States Patent
Suzuki

(10) Patent No.: US 9,332,953 B2
(45) Date of Patent: May 10, 2016

(54) SUPERVISED MACHINE LEARNING TECHNIQUE FOR REDUCTION OF RADIATION DOSE IN COMPUTED TOMOGRAPHY IMAGING

(71) Applicant: THE UNIVERSITY OF CHICAGO, Chicago, IL (US)

(72) Inventor: Kenji Suzuki, Homewood, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 14/423,997

(22) PCT Filed: Aug. 30, 2013

(86) PCT No.: PCT/US2013/057641
§ 371 (c)(1),
(2) Date: Feb. 25, 2015

(87) PCT Pub. No.: WO2014/036473
PCT Pub. Date: Mar. 6, 2014

(65) Prior Publication Data
US 2015/0201895 A1    Jul. 23, 2015

Related U.S. Application Data

(60) Provisional application No. 61/695,698, filed on Aug. 31, 2012.

(51) Int. Cl.
*A61B 6/00* (2006.01)
*G06T 3/40* (2006.01)
*G06T 5/00* (2006.01)
(Continued)

(52) U.S. Cl.
CPC .............. *A61B 6/5211* (2013.01); *A61B 6/032* (2013.01); *A61B 6/488* (2013.01); *A61B 6/5282* (2013.01); *A61B 6/542* (2013.01); *A61B 6/545* (2013.01); *G06K 9/66* (2013.01); *G06T 3/4046* (2013.01); *G06T 5/002* (2013.01); *G06T 5/50* (2013.01); *G06T 11/008* (2013.01); *G06T 2207/10081* (2013.01); *G06T 2207/30028* (2013.01); *G06T 2207/30061* (2013.01)

(58) Field of Classification Search
CPC ................... A61N 2005/1061; A61N 5/1071; A61N 5/10; A61B 6/032; A61B 6/4258; A61B 17/1703; G06T 2207/10116; G06T 2207/10081
See application file for complete search history.

(56) References Cited

U.S. PATENT DOCUMENTS 6,016,333 A    1/2000   Kalvin
6,754,380 B1   6/2004   Suzuki et al.
(Continued)

OTHER PUBLICATIONS

Suzuki et al., "Computer-Aided Diagnostic Scheme for Distinction Between Benign and Malignant Nodules in Thoracic Low-Dose CT by Use of Massive Training Artificial Neural Network," 2005, IEEE Tansactions on Medical Imaging, vol. 24, No. 9. pp. 1138-1150.*
(Continued)

*Primary Examiner* — Nirav G Patel
*Assistant Examiner* — Kenny Cese

(57) ABSTRACT

Substantial reduction of the radiation dose in computed tomography (CT) imaging is shown using a machine-learning dose-reduction technique. Techniques are provided that (1) enhance low-radiation dosage images, beyond just reducing noise, and (2) may be combined with other approaches, such as adaptive exposure techniques and iterative reconstruction, for radiation dose reduction.

23 Claims, 7 Drawing Sheets

(51) Int. Cl.
*G06T 5/50* (2006.01)
*A61B 6/03* (2006.01)
*G06T 11/00* (2006.01)
*G06K 9/66* (2006.01)

(56) References Cited

U.S. PATENT DOCUMENTS

| | | | |
|---|---|---|---|
| 6,819,790 | B2 | 11/2004 | Suzuki et al. |
| 7,545,965 | B2 | 6/2009 | Suzuki et al. |
| 2006/0018524 | A1 | 1/2006 | Suzuki et al. |
| 2010/0020208 | A1* | 1/2010 | Barbu .................... G06K 9/40 348/250 |
| 2010/0067772 | A1* | 3/2010 | Kitamura ............... A61B 6/482 382/132 |
| 2010/0177943 | A1 | 7/2010 | Zhao et al. |
| 2011/0268334 | A1 | 11/2011 | Ra et al. |
| 2013/0051516 | A1* | 2/2013 | Yang ....................... A61B 6/03 378/4 |
| 2013/0116554 | A1* | 5/2013 | Kaiser ................ A61K 49/0438 600/425 |

OTHER PUBLICATIONS

Goodband et al. "Artifical Neural Networks in Radiation Therapy," Intelligent and Adaptive Systems in Medicine, 2008, pp. 213-257.*
International Search Report and Written Opinion, International Application No. PCT/US2013/057641, mailed Dec. 13, 2013.
Suzuki, Pixel-based machine learning in medical imaging, Int. J. Biomed. Imaging, 18 pp. (2012).

* cited by examiner

*Figure 4B* Corresponding HD-like CT output image of the trained MTANN converter (SNR$_{ave}$ = 14.3 dB)
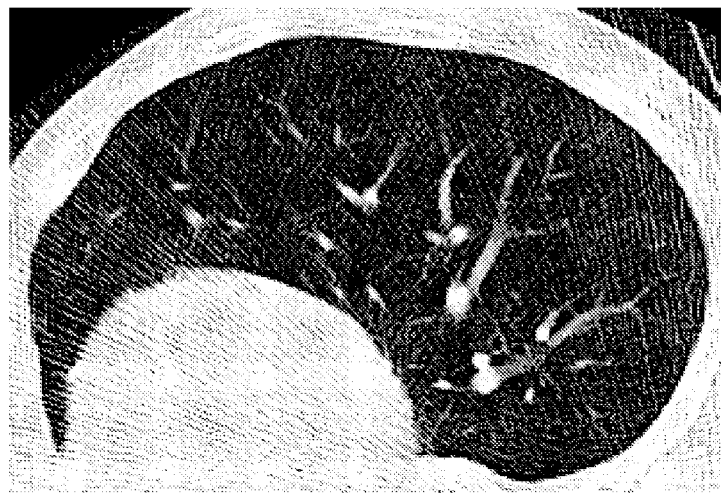
*Figure 4A* Original ULDCT (0.1 mSv) image (SNR$_{ave}$ = 3.4 dB)

Corresponding HD-like CT output image of the trained MTANN converter (SNR$_{ave}$= 14.3 dB)

Original ULDCT (0.1 mSv) image (SNR$_{ave}$= 3.4 dB)

Reference HDCT (1.5 mSv) image
(SNR$_{ave}$ = 16.9 dB ± 1.4 dB)

ULDCT (0.1 mSv) image
(SNR$_{ave}$ = 5.4 dB ± 2.6 dB)

SUPERVISED MACHINE LEARNING TECHNIQUE FOR REDUCTION OF RADIATION DOSE IN COMPUTED TOMOGRAPHY IMAGING

CROSS-REFERENCE TO RELATED APPLICATIONS

This application claims the benefit of U.S. application Ser. No. 61/695,698, filed Aug. 31, 2012, entitled "Supervised Machine Learning Technique For Reduction Of Radiation Dose In Computed Tomography Imaging," which is hereby incorporated by reference in its entirety.

FIELD OF THE INVENTION

The invention relates generally to the field of medical imaging and more particularly to techniques for converting low-dose quality computed tomography images into higher quality computed tomography images.

BACKGROUND

Computed tomography (CT) and various, other medical imaging techniques have been used to detect cancer in patients. CT images, for example, allow medical personnel to screen for tissue anomalies, classifying them based on indicators such as abnormal or normal, lesion or non-lesion, and malignant or benign. Conventional CT image analysis and interpretation and cancer detection and diagnosis techniques involve a radiologist assessing volumes of CT image data of a subject tissue. Given the volume of data, however, it can be difficult to identify and fully assess CT image data for cancer detection. CT image analysis is known to result in mis-diagnoses in some instances, resulting from false positive determinations that lower overall efficiency of CT image analysis as a viable detection technique. There are automated techniques for CT image analysis, e.g., automated techniques for detecting lung nodules in CT scans. Yet, these automated techniques are nonetheless limited and, as with non-automated techniques, are benefited by using higher dose CT imaging for data collection for better image quality.

For CT image analysis, interpretation, detection and diagnosis, there is a tradeoff between radiation dosage levels and image quality. Generally, higher radiation doses result in higher signal-to-noise ratio, higher resolution images with fewer artifacts, while lower doses lead to increased image noise, more artifacts and less-sharp images. The higher radiation may, though, increase the risk of adverse side effects, e.g., increasing the risk of radiation-induced cancer. As a result, low dose radiation CT has been studied of late, with the hope of improving image analysis and detection, without increasing the chances of potential adverse side effects.

Yet, despite recent developments in radiation dose reduction techniques in CT scanning, e.g., techniques such as adaptive exposure and iterative reconstruction, current radiation dosing is still very high, especially for screening populations. As such, there continues to be public concern about radiation risks from current CT testing levels. In response, the techniques of the present invention provide a way of using low-dose CT imaging with vastly improved, higher-dose like image quality.

SUMMARY OF THE INVENTION

Techniques for converting low-dose (LD) CT images to higher quality, lower noise images, such as for example higher-dose (HD) like CT images, are provided. The techniques rely upon supervised machine-learning techniques trained with input low-dose (LD) CT images and corresponding "teaching" higher-dose (HD) CT images with less noise or fewer artifacts. Through training, the machine-learning techniques learn the relationship between the input and teaching images, allowing the conversion of lose-dose CT images into HD-like CT images. Once trained, the machine-learning technique no longer requires further training, high-dose CT images. Rather the system is trained to produce, in an ongoing manner, HD-like CT images from low-dose CT images.

BRIEF DESCRIPTION OF THE DRAWINGS

FIG. 4a is a depiction of an input image of a non-trained ultra-ultra low dosage CT image; and FIG. 4b is a depiction of an output image of a trained HD-like CT image produced from the image of FIG. 3a, using a massive-training artificial neural network (MTANN) technique, in accordance with an example.

DETAILED DESCRIPTION

Figure 1:
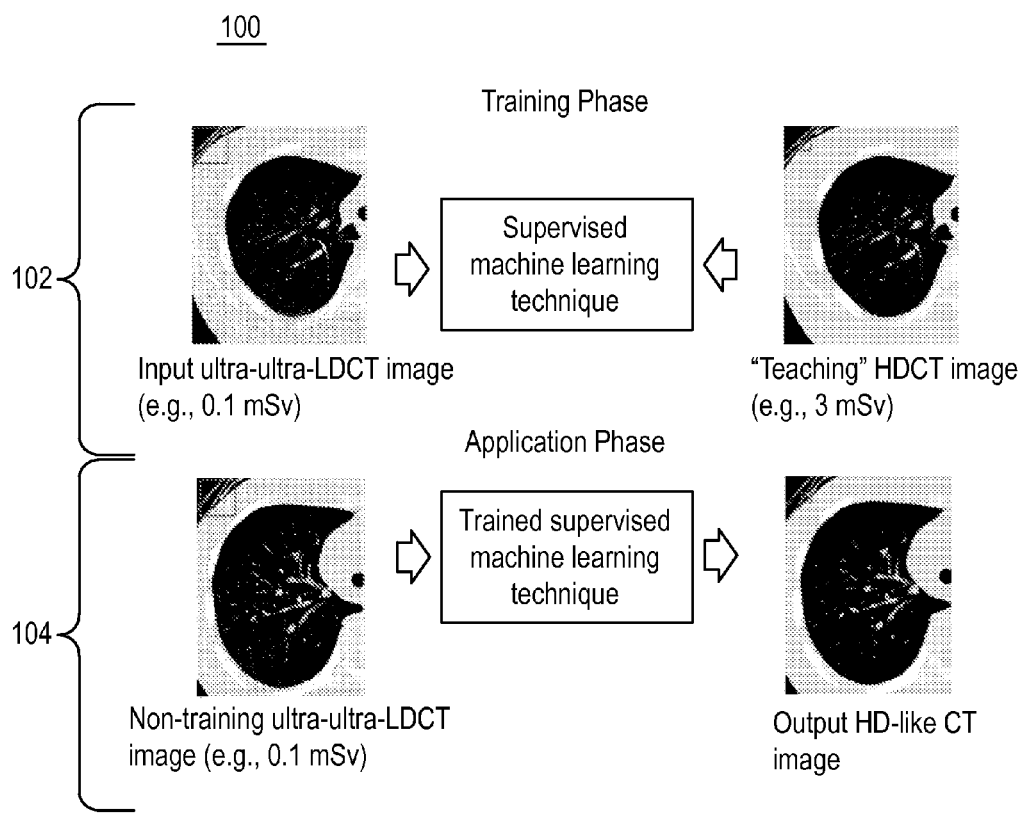
FIG. 1 illustrates a training phase and application phase process of a supervised dose reduction technique, in accordance with an example.

A schematic diagram of example training and application for a supervised dose reduction technique 100 is shown in FIG. 1. The supervised dose reduction technique developed herein is able to produce high-quality medical images from lower-quality medical images through the use of a training phase, that once completed can be used repeatedly on follow-up images for automatically converting lower-quality images to high-quality images. As discussed herein, various supervised machine learning techniques may be used to form the image conversion engines described herein. While the image conversion engines may be designed to effect image conversion from a low-quality image to a higher-quality image based on any number of image characteristics, as provided herein, in some examples, the conversion engine is particularly configured to reduce noise in the lower-quality image and preserve and enhance signal (such as edge and lesion) pixel depictions in the final, converted image. By altering the noise characteristics, for example through dramatic (10-fold or more) noise reduction, the conversion engine is able to output higher-quality images that allow for such. In some examples described herein, an image conversion engine is used to convert images such as low-dose CT images (LDCT) to high-dose-like CT images (HDCT), through an initial training phase that need only be performed once, in some examples. FIG. 1 shows both a training phase 102, in which the supervised dose reduction technique is developed for image conversion, and a post-training, application phase 104, in which the learned image conversion is used. In all, the techniques allow for the use of lower, more acceptable radiation dosages for CT imaging.

The techniques are described herein using CT imaging as an example, converting low radiation dosage taken images to lower noise, fewer artifact images, resembling those taken with high radiation dosages. But it will be appreciated that the learning techniques herein may be implemented with any number of medical imaging techniques amenable to low and high quality image taking, for example ultrasound imaging, two-dimensional x-ray imaging, nuclear imaging, tomosynthesis imaging and magnetic resonance imaging.

With respect to FIG. 1, in the training phase, a supervised dose reduction technique is trained with different types of "input" images/volumes and corresponding "teaching" images/volumes. The "input" images, in the illustrated example, are images that are of a lower quality, such as low dose CT images. The "teaching" images are of higher quality images, such as high dose CT images. The "input" images and the "teaching" images are preferably corresponding images, in that they are images of the same tissue region. In some examples, the correspondence may be exact, e.g., taken at the same time or right after one another of the same subject, e.g., a human patient. In other examples, the images may correspond but be taken at different magnifications or merely partially overlap. In such cases image registration, expansion/reduction, and alignment may be used to make the "input" images and the "teaching" images properly correspond for data analysis. While images are discussed, it will be understood that such images may be two dimensional (2D) images, three dimensional (3D) images or volumetric data from which various 2D and 3D images can be formed. In certain embodiments, the image data can be four dimensional, varying, for example, as a function of time. Thus, as used herein images (or the phrase images/volumes) refers to any of these data types.

Figure 2:
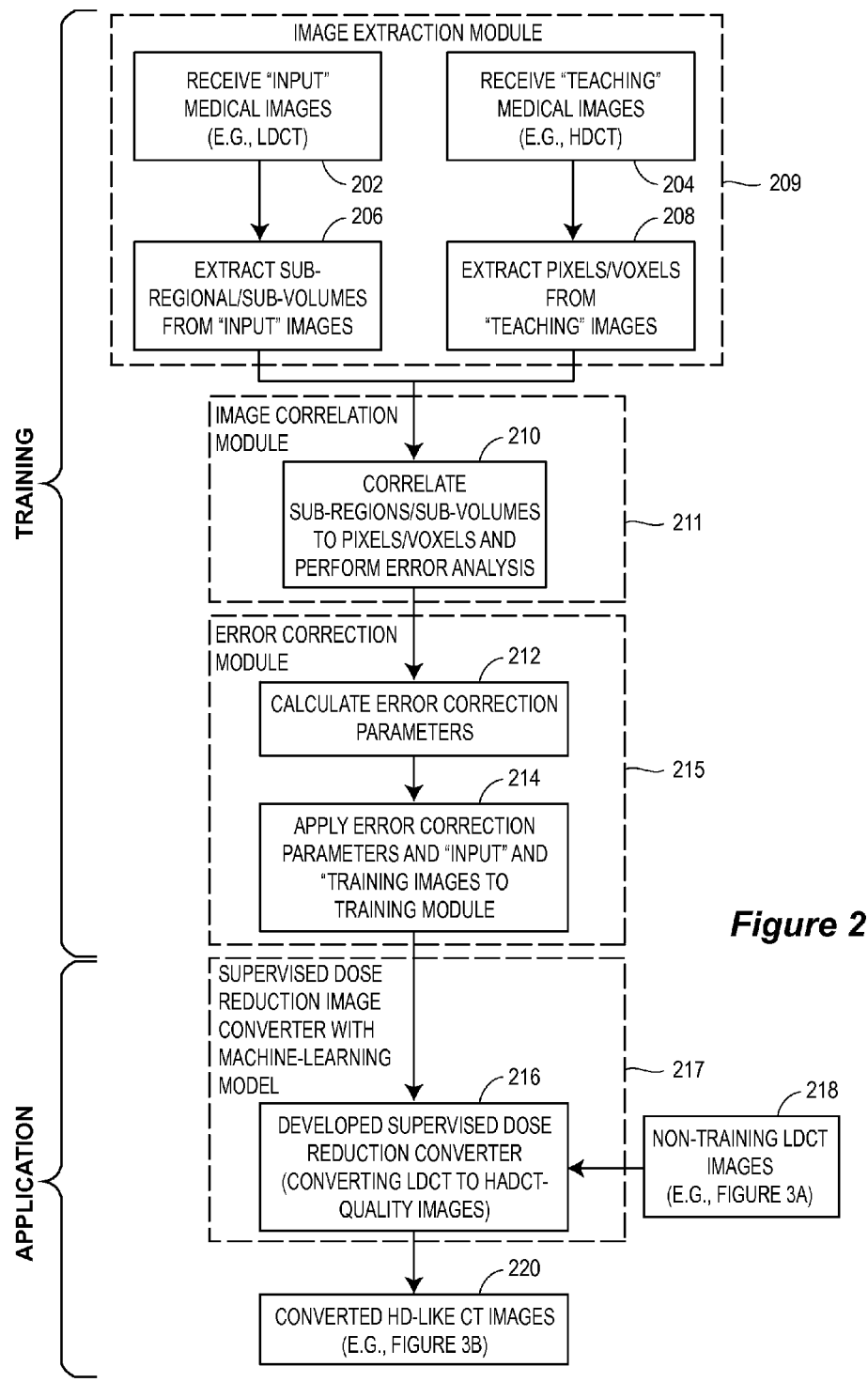
FIG. 2 is a flow diagram of a process for developing a supervised dose reduction technique, in accordance with an example.

FIG. 2 illustrates an example flow diagram of a process 200 for performing a supervised dose reduction technique, and showing two initial stages obtaining "input" medical images (stage 202) and "teaching" medical images (stage 204), respectively. Once the image types are obtained they may be provided to a supervised machine learning technique, as shown in FIG. 1, for converting lower quality images, e.g., LDCT images with noise and artifacts, into high quality images, e.g., HD-like CT images with less noise or fewer artifacts. The number of "input" images may be comparatively small, 1, 10 or less, or 100 or less, by way of example. The number of "training" images have be small as well, 1, 10 or less, 20, or 50 or less. However, a larger number of "training" images may be used as well, 100-1,000 images, 1,000-10,000 images, or more than 10,000 images. The number of training images used may be adjusted from a small number to a high number based on the size of the "input" image, the desired reduction in SNR on the converted "input" image, the desired resolution of the edge effects on the converted "input" image, the number of and variation in the likely edges in the "input" image, the desired signal contrast on the converted "input" image, the radiation dose of the "input" image, the number of prior CT scans of a patient (accumulated radiation dose level), and the processing load on the computer system performing the comparisons.

Figure 7:
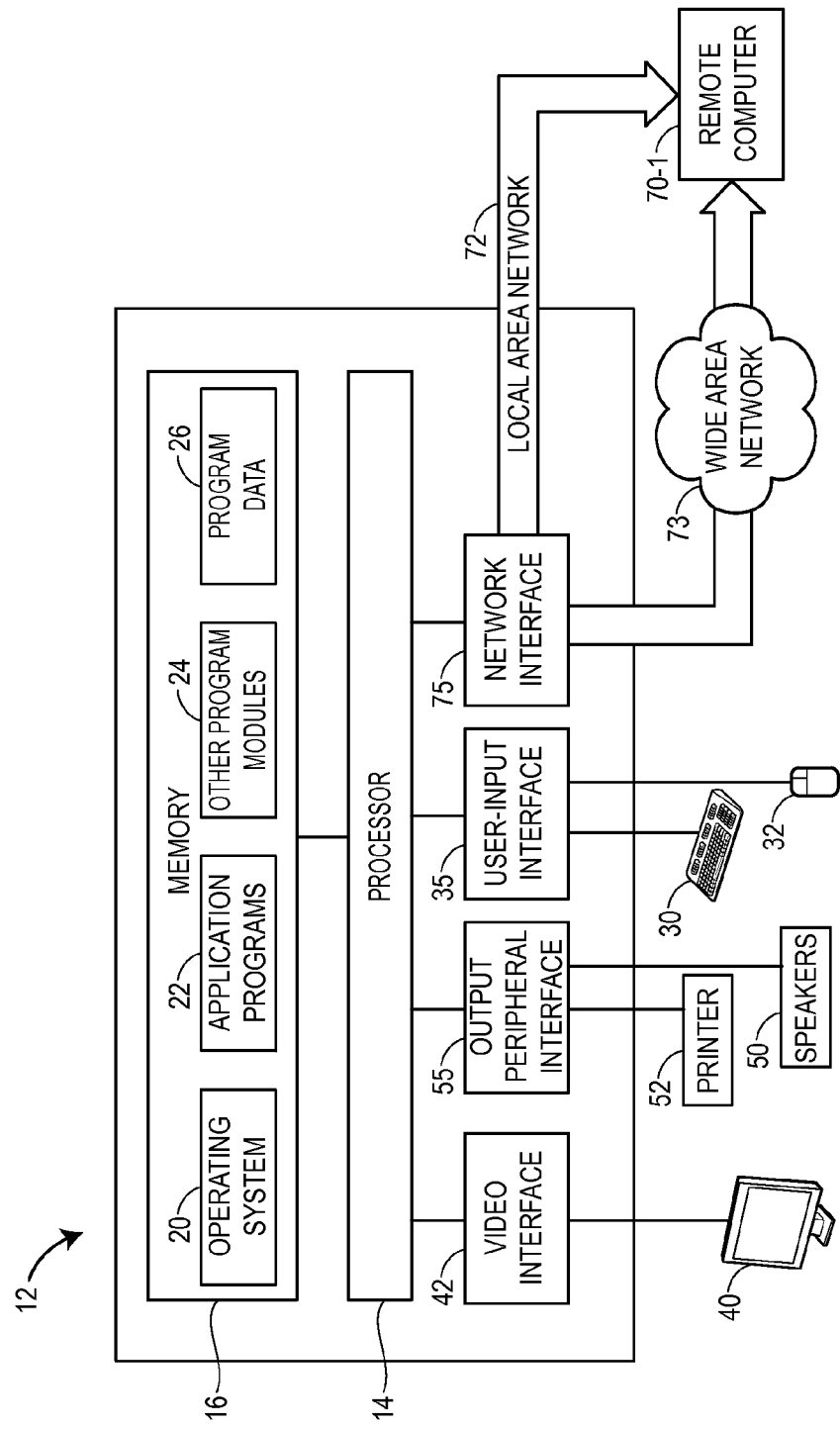
FIG. 7 is a system for performing supervised dose reduction techniques, in accordance with an example.

To develop an image converter, a large number of pixel/voxel regions may be obtained over both image types, from stages 202 and 204. For example, as shown in FIG. 2, overlapping sub-regions/sub-volumes may be extracted from the "input" LDCT images, at a block 206, and numerous single pixel or sub-regions/sub-volumes may be extracted from the corresponding "teaching" HDCT images, as teaching values, at a block 208. Example sub-regions/sub-volumes and pixels are shown in FIG. 1. The supervised dose reduction technique may be trained by use of a large number of input sub-regions/sub-volumes together with each of the corresponding teaching single pixels, where the larger the number of these the greater the potential for noise reduction and signal (such as edge and lesion) resolution improvement. An image extraction module 209 may perform these operations, in hardware, software, or some combination thereof. For example, the image extraction module 209 may be stored in a non-transitory computer readable medium, such as a computer memory, for execution by a processor, as shown in FIG. 7.

As illustrated in FIG. 2, and also as part of the supervised machine learning technique, the extracted sub-regions/sub-volumes and pixels are correlated, after which an error analysis is performed, at a block 210. The correlating of derived pixels, voxels, sub-regions, and/or sub-volumes may be performed by an image correlation module 211 that may be stored in a non-transitory computer readable medium, such as a computer memory, for execution by a processor, as shown in FIG. 7. The error to be minimized by training of the supervised dose reduction technique can be defined by any error measures between output pixel/voxel values and teaching (or desired) pixel/voxel values. Example error measures include a root mean square error, a mean square error, a mean absolute error, a Mahalanobis distance measure, and similarity measures such as mutual information. Example pixel/voxel based comparisons as may be used for error detection are described further below and in Kenji Suzuki, *Pixel-Based Machine Learning in Medical Imaging*, International Journal of Biomedical Imaging, Vol. 2012, Article ID 792079, 2012, which is expressly incorporated by reference, in its entirety. Various pixel/voxel-based machine learning (PML) techniques may be applied as described herein, these include neural filters, neural edge enhancers, neural networks, shift-invariant neural networks, artificial neural networks (ANN), including massive-training ANN (MTANN), massive-training Gaussian process regression, and massive-training support vector regression (MTSVR), by way of examples. Additional techniques for error analysis and medical image data comparisons between an "input" image and a "training" image include those provided in U.S. Pat. Nos. 6,754,380, 6,819,790, and 7,545,965, and U.S. Publication No. 2006/0018524, the entire specifications of all of which are hereby incorporated by reference, in their respective entireties.

Once the error analysis is performed, as shown in FIG. 2, error correction parameters are determined (via block 212) for use in correcting image conversions of errors, whether from patient-related characteristics or equipment-related characteristics. The error correction parameters are passed to a training model engine (via block 214), along with the "input" images and "training" images from which a supervised dose reduction converter is constructed capable of converting LDCT images to HDCT-quality images, as shown in FIGS. 1 and 2. An error correction module 215, which may be stored in a non-transitory computer readable medium, such as a computer memory, for execution by a processor, as shown in FIG. 7, may perform the blocks 212 and 214.

A supervised dose reduction converter is trained, at a block 216, by using a training algorithm for the machine-learning model developed at block 214. A training module 217, which may be stored in a non-transitory computer readable medium, such as a computer memory, for execution by a processor, as shown in FIG. 7, may perform the training of block 216. When the machine-learning model is a multi-layer perceptron, an error back-propagation (BP) algorithm can be used. When the machine-learning module is a linear-output artificial neural network (ANN) regression (see, for example, Suzuki, *Pixel-Based Machine Learning in Medical Imaging*, International Journal of Biomedical Imaging, Vol. 2012, Article ID 792079 incorporated by reference herein), a linear-output BP algorithm can be used. After training, the supervised dose reduction converter (block 216) is able to assess sub-regions/sub-volumes of incoming non-training input images (from block 218) and convert those to output pixel/voxel values and resulting images (at block 220) similar to or close to the corresponding values as would appear in an HDCT image of the same corresponding structures. Thus, the supervised dose reduction technique acquires the function of converting LDCT images with noise and artifacts into HD-like CT images with less noise or fewer artifacts, as in the illustrated examples.

Figure 3B:
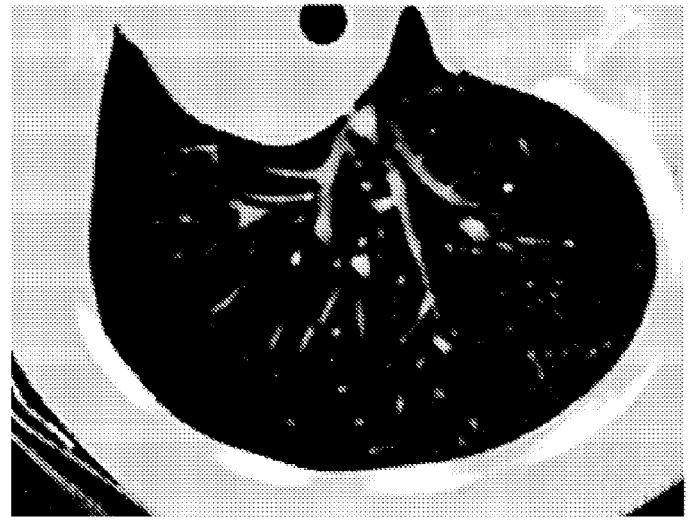
FIG. 3b is a depiction of an output image of a HD-like CT image produced from the image of FIG. 3a, in accordance with an example.
Figure 3A:
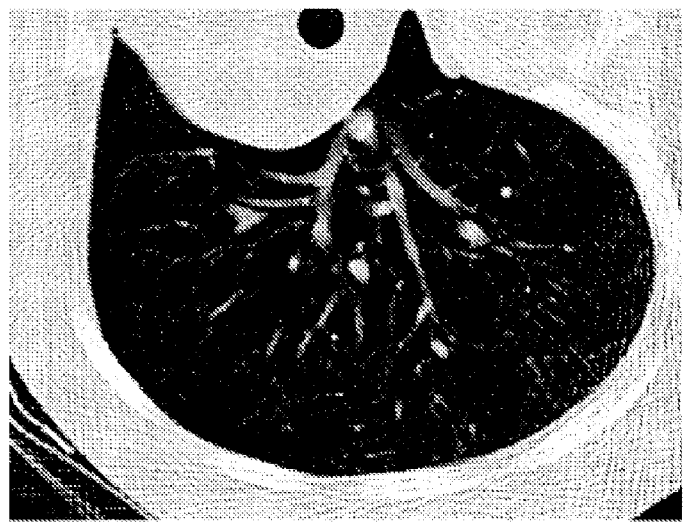
FIG. 3a is a depiction of an input image of a non-trained ultra-ultra low dosage CT image.

FIG. 3a illustrates an example of conversion of a non-training, input lower quality image, in this case an LDCT image. The image taken with a dosage of 0.1 mSv is characterized by relatively high noise, e.g., having a signal-to-noise ratio (SNR) of 4.2 dB and various spurious artifacts. The same image after conversion to a higher quality image, in this case an HDCT-like image having a much higher SNR of 9.7 dB, is provided in FIG. 3b. The 4.5 dB improvement in SNR corresponds to a 2.8× factor improvement in noise reduction. The enhanced low-dose image produced by the present techniques may have a SNR that is, or is about, 10, 9, 8, 7, 6, 5, 4, 3, 2, or 1 dB higher than the original low-dose image, by way of example.

The supervised dose reduction converter shown in FIG. 2 may include a machine-learning model, such as a linear-output ANN regression model, a support vector regression model, decision trees, supervised nonlinear regression, nearest neighbor algorithm, association rule learning, inductive logic programming, reinforcement learning, representation learning, similarity learning, sparse dictionary learning, manifold learning, dictionary learning, boosting, Bayesian networks, case-based reasoning, Kernel machines, subspace learning, Naive Bayes classifiers, ensemble learning, statistical relational learning, a nonlinear Gaussian process regression model (which is capable of operating on pixel/voxel data directly), and the like. The linear-output ANN regression model, for example, preferably employs a linear function instead of a sigmoid function as the activation function of the unit in the output layer, because the characteristics of an ANN are improved significantly with a linear function when applied to the continuous mapping of values in image processing. Note that the activation functions of the units in the hidden layer are a sigmoid function for nonlinear processing, and those of the unit in the input layer are an identity function, as usual.

For low-dose CT image conversion, the machine-learning models described herein may convert the input image, characterized by a low-dose CT image noise level to a high-dose CT image noise level, for example through applying a trained noise suppression on identified sub-regions or sub-volumes of the input image. The machine-learning models may further apply a trained edge preservation on the low-dose CT image as well. This preservation may use noise reduction as described herein, but may also include edge enhancement as described in Suzuki, *Pixel-Based Machine Learning in Medical Imaging*, International Journal of Biomedical Imaging, Vol. 2012, Article ID 792079 incorporated by reference herein, such as neural edge enhancers and ANN (including MTANN) edge enhancers. In some such examples, the resulting enhanced low-dose CT image will have both a noise level characteristic of what is generally considered high-dose CT image noise levels and an edge contrast that is also characteristic of what is generally considered high-dost CT image edge contrast or resolution.

In some further examples, the machine-learning module may be integrated into existing image processing systems. For example, the machine-learning module of the supervised dose reduction converter may be integrated with a machine-learning classification model, such as a multi-layer perceptron, a support vector machine, linear discriminant analysis, or quadratic discriminant analysis. In some examples, such incorporation of a classification model may affect performance of the supervised dose reduction technique, because a machine learning classification model is not designed to output continuous values, but binary classes (or nominal categories). The pixel/voxel values of the input images/volumes may be normalized from 0 to 1. The input to the supervised dose reduction technique consists of pixel/voxel values in a subregion/subvolume extracted from an input LDCT image/volume. The output of the supervised dose reduction technique is a continuous scalar value, which is associated with the center voxel in the subregion/subvolume. The entire output image/volume is obtained by scanning with the input subvolume of the supervised dose reduction technique on the entire input LDCT image/volume.

In an example test implementation of the present techniques, instead of using real LDCT images, simulated LDCT images were used. For example, simulated LDCT images were formed by degrading real HDCT images, and using these degraded images as input images to the supervised dose reduction technique. The major noise in LDCT images was quantum noise. Simulated quantum noise (which can be modeled as signal-dependent noise) is added to high-radiation-dose sinograms, $f_O(\xi, \phi)$, acquired at a high radiation dose level, represented by $$f_N(\xi,\phi)=f_O(\xi,\phi)+n\{\sigma(f_O(\xi,\phi))\}, \quad (1)$$

where $\phi$ is a projection angle, $\xi$ is distance from the center along the projection angle, $n\{\sigma(f_O(\xi, \phi))\}$ is noise with standard deviation $\sigma\{f_O(\xi, \phi)\}=\sqrt{f_O(\xi,\phi)}$, and $k_N$ is a parameter determining the amount of noise. Simulated low-radiation-dose sinograms obtained with this method used for creating simulated LDCT images by using a reconstruction algorithm such as filtered back projection or an iterative reconstruction algorithm. Similarly, HDCT images are reconstructed from original HD sinograms. Instead of the above quantum noise model alone, a more realistic stochastic noise model can be used. In addition to the quantum noise, the stochastic noise model may include energy-integrating detectors, tube-current modulation, bowtie beam filtering, and electronic system noise. Alternatively, simulated LDCT images can be obtained by using a LDCT simulator in a CT system.

Experiment

To train the supervised dose reduction technique, i.e., final image converter in FIG. 2, 6 sets of CT images of a chest phantom (Kyoto Kagaku, Kyoto, Japan) were acquired with a tube voltage of 120 kVp, tube current of 10, 25, 50, 100, 150, and 300 mA, and a collimation of 5 mm. CT images were reconstructed with the lung reconstruction kernel. Each reconstructed CT image had a matrix size of 512×512 pixels with no overlap between slices. A 10 mA (0.1 mSv) ultra-ultra-LDCT image and the corresponding 300 mA (3 mSv)

HDCT image were used for training the supervised dose reduction technique as the input image and teaching image, respectively. We evaluated the image quality of CT images using signal-to-noise ratio (SNR) in each image with use of corresponding 3 mSv HDCT images as the reference standard. With the trained machine-learning dose reduction technique, noise and artifacts in ultra-ultra-low-dose CT images (0.1 mSv) were reduced substantially, while details of soft-tissue opacities such as pulmonary vessels and bony structures were maintained. The SNR of 0.1 mSv ultra-ultra-low-dose CT images was improved from 4.2 to 9.7 dB. The processing time is very short. The processing time for each image was 0.8 sec on a PC (AMD Athlon, 3.0 GHz). With the supervised machine-learning dose-reduction technique, the image quality of 0.1 mSv ultra-ultra-low-dose CT images was improved substantially to the quality comparable to 0.5-1.0 mSv CT images; thus, radiation dose can potentially be reduced by 80-90%.

Figure 5B:
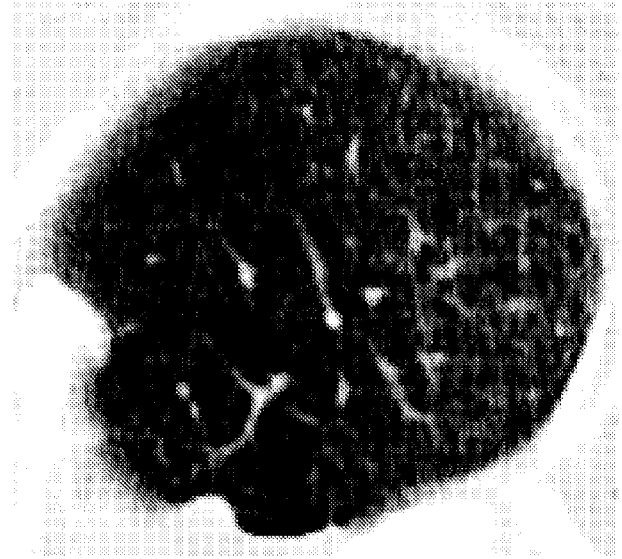
FIG. 5b is a depiction of an output image of a trained HD-like CT image produced from the image of FIG. 3a, using a MTANN technique, in accordance with another example.
Figure 5A:
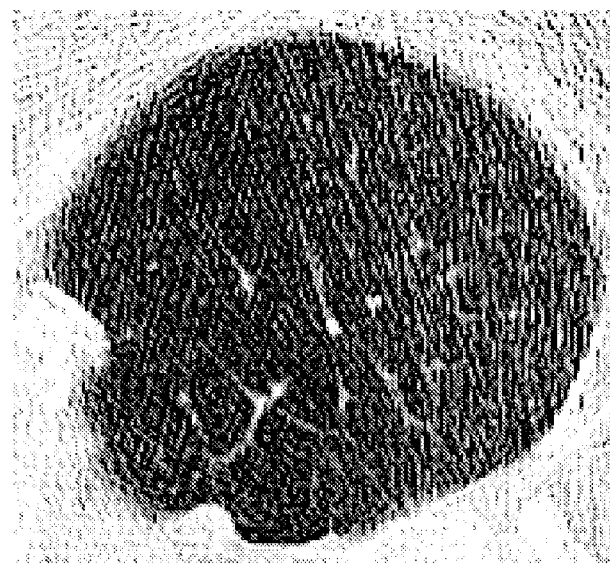
FIG. 5a is a depiction of an input image of a non-trained ultra-ultra low dosage CT image.
Figure 6B:
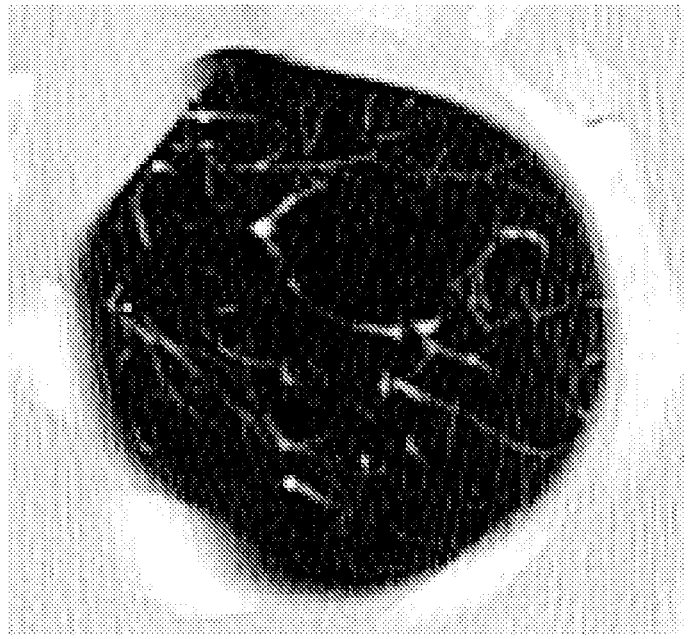
FIG. 6b is a depiction of a reference HD-like CT image produced at a high dose level than that of FIG. 6a, in accordance with another example.
Figure 6A:
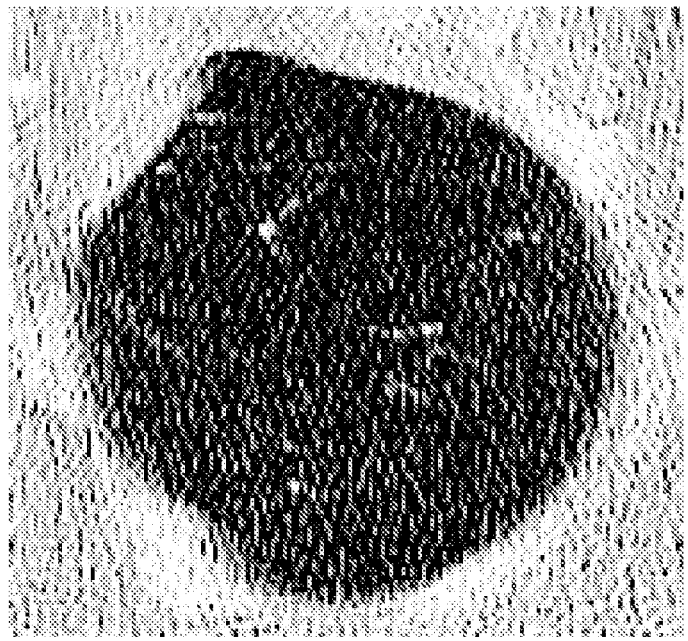
FIG. 6a is a depiction of an input image of a non-trained ultra-ultra low dosage CT image.

To evaluate the generalizability of the supervised dose reduction technique, we acquired ultra-ultra-LDCT (UL-DCT) scans of 3 human patients with a tube voltage of 120 kVp and a tube current of 10 mA. The effective radiation dose of an ULDCT study was 0.1 mSv. We evaluated the image quality of CT images by using signal-to-noise ratio (SNR) in each image. We applied the supervised dose reduction technique trained with the phantom to the patient cases. With the trained supervised dose reduction technique, noise and artifacts (e.g., streaks) in ULDCT images (0.1 mSv) were reduced substantially, while details of soft tissue such as pulmonary vessels and bones were maintained, as illustrated in FIGS. 4a/4b, 5a/5b, and 6a/6b. In these example implementation, the average SNR for the 0.1 mSv ULDCT images for patients was improved from 2.3 (±1.8) to 13.0 (±2.5) dB (two-tailed t-test; P<0.05). This 10.7 dB average SNR improvement was comparable to the 11.5 dB improvement that we were able to achieve by increasing the effective radiation dose from 0.1 mSv (10 mA) to 1.5 mSv (150 mA) in the phantom study, used as a reference, as illustrated by comparing FIGS. 5a/5b and 6a/6b. That is, in this example implementation we show that the with the supervised dose reduction technique, the image quality of 0.1 mSv ULDCT was improved substantially to the quality comparable to 1.5 mSv HDCT. Thus, radiation dose can potentially be reduced by 93%, as shown in this example. Radiation dose reductions of between 90% to 95% reduction may thus be achieved. In other examples, and depending on the desired changed in SNR for the input images (ULDCT or otherwise), dose reductions below 95% may be achieved, including reductions of between 80% to 90%, 70% to 80%, 60% to 70%, or below may be achieved. This dose reduction, without reduction in converted image quality, provides a substantial benefit in CT imaging, especially when one considers iterative imaging exposure and reconstruction for patients and radiologists.

As illustrated in FIG. 2 the example techniques described herein may be implemented in a medical imaging system, such as a CT scanner, e.g., through an image processing portion thereof, or from a separate image processing system. An example set of modules are shown in FIG. 2 and include an image extraction module, an image correlation module, an error correction module, and the supervised dose reduction image converter, which includes the trained machine-learning module.

The techniques herein may be implemented on a computer system, such as shown in FIG. 7. The techniques described herein (e.g., in FIG. 2) may be coded, in software, hardware, firmware, or combination thereof, for execution on a computing device such as that illustrated in FIG. 7. Generally, FIG. 7 illustrates an example of a suitable computing system environment 10 to interface with a medical professional or other user to analyze medical imaging data. It should be noted that the computing system environment 10 is only one example of a suitable computing environment and is not intended to suggest any limitation as to the scope of use or functionality of the method and apparatus of the claims.

With reference to FIG. 7, an exemplary system for implementing the blocks of the claimed method and apparatus includes a general-purpose computing device in the form of a computer 12. Components of computer 12 may include, but are not limited to, a processing unit 14 and a system memory 16. The computer 12 may operate in a networked environment using logical connections to one or more remote computers, such as remote computer 70-1, via a local area network (LAN) 72 and/or a wide area network (WAN) 73 via a modem or other network interface 75. The remote computer 70-1 may include other computers like computer 12, but in some examples, the remote computer 70-1 includes one or more of a medical imaging system, such as (i) an MRI imaging system, (ii) a CT imaging system, (iii) a PET imaging system, and (iv) a medical records database systems. In such examples, computer 12 may be a separate image processing computer, or the computer 12 may reflect part of the medical imaging system. For example, the computing system 10 may be part of a CT scanner medical imaging system. In some examples, the computing system 10 is a remote computer receiving image data from a remote computer 70-1 as a CT scanner medical imaging system. In some examples, the computer system 10 programs a CT scanner medical imaging system, operating as the remote computer 70-1, through network 72 or network 73.

Computer 12 typically includes a variety of computer readable media that may be any available media that may be accessed by computer 12 and includes both volatile and non-volatile media, removable and non-removable media. The system memory 16 includes computer storage media in the form of volatile and/or nonvolatile memory such as read only memory (ROM) and random access memory (RAM). The ROM may include a basic input/output system (BIOS). RAM typically contains data and/or program modules that include operating system 20, application programs 22, other program modules 24, and program data 26. The computer 12 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 12 through input devices such as a keyboard 30 and pointing device 32, commonly referred to as a mouse, trackball or touch pad. Other input devices (not illustrated) may include a microphone, joystick, game pad, satellite dish, scanner, or the like. These and other input devices are often connected to the processing unit 14 through a user input interface 35 that is coupled to a system bus, but may be connected by other interface and bus structures, such as a parallel port, game port or a universal serial bus (USB). A monitor 40 or other type of display device may also be connected to the processor 14 via an interface, such as a video interface 42. In addition to the monitor, computers may also include other peripheral output devices such as speakers 50 and printer 52, which may be connected through an output peripheral interface 55.

Images may be handled using the Digital Imaging and Communications in Medicine (DICOM) format, for example. Images may be stored in a picture archiving and communication system (PACS).

Generally, the techniques herein may be coded in any computing language for execution on computer 12. Image data may be obtained from the remote computer 70-1 and stored loaded on to any of the computer storage devices of computer 12. Once the image data, including image segments, is obtained, a user may input or select the condition parameters through an input mechanism as described. Although, in other examples, the condition parameters may be pre-selected or automatically determined, for example, based on a particular type of analysis that is to be performed. The output of the executable program may be displayed on a display (e.g., a monitor 40), sent to a printer 52, stored for later use by the computer 12, or offloaded to another system, such as one of the remote computers 70. The output may be in the form of an image or image data from which one or more images may be created. Operations of the system may be recorded in a log database for future reference. This log database, which may be accessible through either network 72 or 73 may be accessed at subsequent times when a post-RT image is to be obtained, for example.

More generally, the various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed:

1. A method, comprising:
   obtaining, from a scanner, first computed tomography (CT) image information for scanning of a first article at a first radiation dosage level,
   wherein the first CT image information exhibits one of a first noise level or a first image signal contrast;
   applying, in a processor, signal processing to the first CT image information, the applied signal processing based on a machine-learning model trained using CT training images, wherein the CT training images correspond to scanning of one or more second articles at each of the first radiation dosage level and a second radiation dosage level higher than the first radiation dosage level; and
   producing, from the processor as a result of the applied signal processing, second CT image information that exhibits one of a second noise level lower than the first noise level or a second image signal contrast higher than the first image signal contrast.

2. The method of claim 1, further comprising:
   displaying an image derived from the second CT image information.

3. The method of claim 1, wherein the applied signal processing comprises at least one of:
   noise suppression applied to portions of the first CT image information corresponding to a plurality of one of a sub-region or a sub-volume, the noise suppression determined at least in part based on the one or more CT training images corresponding to scanning of second articles at the second radiation dosage level; and
   edge enhancement applied to the portions of the first CT image information corresponding to the plurality of one of a sub-region or a sub-volume, the edge enhancement determined at least in part based on the one or more CT training images corresponding to scanning of second articles at the second radiation dosage level.

4. The method of claim 1, wherein the machine-learning model comprises at least one of a linear-output artificial neural network (ANN) regression model, a support vector regression model, or a nonlinear Gaussian process regression model.

5. The method of claim 4, wherein the machine-learning model is the linear-output ANN regression model and produces a linear function as an activation function for continuous mapping of the first CT image information to the second CT image information.

6. The method of claim 1, wherein the applied signal processing is based on a machine-learning classification model.

7. The method of claim 6, wherein the machine-learning classification model is at least one of a multilayer perceptron, a support vector machine, a linear discriminant analysis machine, or a quadratic discriminant analysis machine.

8. The method of claim 1, wherein the second CT image information has a signal-to-noise ratio of at least twice a signal-to-noise ratio of the first CT image information.

9. The method of claim 1, wherein the first radiation dosage level is 0.1 milliseverts (mSv) or less.

10. The method of claim 9, wherein the second radiation dosage level is 3 mSv.

11. The method of claim 1, wherein the second CT image information corresponds to an image quality obtained by scanning the first article at a radiation dosage level of between 0.5 and 1.0 milliseverts (mSv).

12. The method of claim 1, wherein the first radiation dosage level corresponds to a radiation reduction of at least 90% over the second radiation dosage level.

13. The method of claim 1, wherein the second CT image information exhibits an average signal-to-noise ratio (SNR) improvement of at least 10 decibels (dB) over the first CT image information.

14. The method of claim 1, wherein an estimated effective dosage range corresponds to a body region scanned to obtain the CT image information, and wherein the first radiation dosage level is within a lowest quarter of the estimated effective dosage range.

15. The method of claim 1, wherein an estimated effective dosage range corresponds to a body region scanned to obtain the CT image information, and wherein the first radiation dosage level is within a lowest 10% of the estimated effective dosage range.

16. The method of claim 1, wherein an estimated effective dosage range corresponds to a body region scanned to obtain the CT image information, and wherein the first radiation dosage level is within a lowest 5% of the estimated effective dosage range.

17. The method of claim 1, wherein an estimated effective dosage range corresponds to a body region scanned to obtain the CT image information, and wherein the first radiation dosage level is within a lowest 1% of the estimated effective dosage range.

18. An apparatus, comprising:
a memory configured to store first computed tomography (CT) image information obtained by scanning of a first article at a first radiation dosage level, wherein the first CT image information exhibits one of a first noise level or a first image signal contrast; and
a processor coupled to the memory and configured to apply signal processing to the first CT image information, the applied signal processing based on a machine-learning model trained using CT training images, wherein the CT training images correspond to scanning of one or more second articles at each of the first radiation dosage level and a second radiation dosage level higher than the first radiation dosage level,
wherein the applied signal processing produces second CT image information that exhibits one of a second noise level lower than the first noise level or a second image signal contrast higher than the first image signal contrast.

19. The apparatus of claim 18, further comprising:
a display configured to display an image derived from the second CT image information.

20. The apparatus of claim 18, wherein the applied signal processing comprises at least one of:
noise suppression applied to portions of the first CT image information corresponding to a plurality of one of a sub-region or a sub-volume, the noise suppression determined at least in part based on the one or more CT training images corresponding to scanning of second articles at the second radiation dosage level; and
edge enhancement applied to the portions of the first CT image information corresponding to the plurality of one of a sub-region or a sub-volume, the edge enhancement determined at least in part based on the one or more CT training images corresponding to scanning of second articles at the second radiation dosage level.

21. The apparatus of claim 18, wherein the applied signal processing is based upon
a determination of portions of first training CT image information corresponding to a plurality of one of a sub-region or a sub-volume each scanned at a third radiation dosage and a determination of one of pixels or voxels from counterpart portions of second training CT image information scanned at a fourth radiation dosage level higher than the third radiation dosage level, and
a correlation of the determined portions of the first training CT image information with the determined portions of the second training CT image information and an error analysis of the correlated, determined portions of the first and second training CT image information.

22. The apparatus of claim 21, wherein the applied signal processing is based upon error correction parameters derived from the error analysis.

23. A method, comprising:
obtaining, from a scanner, first computed tomography (CT) image information for scanning of a first article at a first radiation dosage level, wherein the first CT image information exhibits one of a first noise level or a first image signal contrast;
applying, in a processor, signal processing to the first CT image information, the applied signal processing based on a machine-learning model trained using CT training images, wherein the CT training images correspond to scanning of one or more second articles at each of the first radiation dosage level and a second radiation dosage level higher than the first radiation dosage level, wherein the first radiation dosage level corresponds to a radiation reduction of at least 90% over the second radiation dosage level; and
producing, from the processor as a result of the applied signal processing, second CT image information that exhibits one of a second noise level lower than the first noise level or a second image signal contrast higher than the first image signal contrast.

* * * * *